(12) United States Patent
Koike et al.

(10) Patent No.: US 7,067,688 B2
(45) Date of Patent: Jun. 27, 2006

(54) ACETYLENE ALCOHOL AND METHOD FOR PREPARING THE SAME

(75) Inventors: Norivuki Koike, Takasaki (JP); Yasunori Sakano, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/269,801

(22) Filed: Nov. 9, 2005

(65) Prior Publication Data
US 2006/0100454 A1 May 11, 2006

(30) Foreign Application Priority Data
Nov. 9, 2004 (JP) .............................. 2004-324877

(51) Int. Cl.
*C07F 7/18* (2006.01)
*C07F 7/08* (2006.01)
*C07F 7/02* (2006.01)

(52) U.S. Cl. .................. 556/482; 556/465; 556/449; 556/466; 556/470; 556/471

(58) Field of Classification Search ................ 556/449, 556/465, 482, 466, 470, 471
See application file for complete search history.

(56) References Cited

U.S. PATENT DOCUMENTS 5,629,387 A  5/1997  Frances et al.
5,708,046 A  1/1998  Jones et al.
6,114,562 A  9/2000  Fukuda et al.

FOREIGN PATENT DOCUMENTS

JP  6-329917 A   11/1994
JP  9-143371 A   6/1997
JP  200-53685 A  2/2000

*Primary Examiner*—Elvis O. Price
(74) *Attorney, Agent, or Firm*—Birch, Stewart, Kolasch & Birch, LLP

(57) ABSTRACT

An acetylene alcohol represented by the following formula,

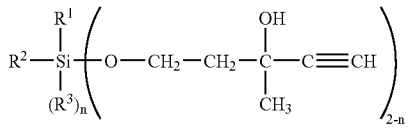

wherein $R^1$ represents a monovalent hydrocarbon radical having 4 to 10 carbon atoms with the carbon atom bonded to the silicon atom being a tertiary carbon, $R^2$ and $R^3$ each represents a monovalent group selected from the group consisting of alkyl groups having 1 to 4 carbon atoms and a fluorinated group represented by the formula, Rf—Q—, wherein Rf is a linear or branched perfluoroalkyl group having 3 to 100 carbon atoms which may be interrupted by one or more ether bonds, and Q is a divalent group having 2 to 10 carbon atoms which may be interrupted by one or more nitrogen, oxygen, or sulfur atoms, and n is zero or 1.

2 Claims, 2 Drawing Sheets

ACETYLENE ALCOHOL AND METHOD FOR PREPARING THE SAME

CROSS REFERENCES

This application claims benefits of Japanese Patent application No. 2004-324877 filed on Nov. 9, 2004 the contents of which are hereby incorporated by reference.

FIELD OF THE INVENTION

The present invention relates to an acetylene alcohol, particularly to an acetylene alcohol having a relatively high molecular weight, and to a method for preparing the same.

DESCRIPTION OF THE PRIOR ART

There are commercially available acetylene alcohols. For example, 3-methyl-1-butyne-3-ol, 3-methyl-1-pentyne-3-ol, 2,5-dimethyl-3-hexyne-2,5-diol are sold under the trade name, Olfine, from Nisshin Chemical Industry Co., and acetylene glycols are sold under the trade name, Surfynol, from Air Products and Chemicals, Inc.

These acetylene alcohols are industrially very important compounds having various uses, for example, as intermediates for chemical synthesis; nonionic surfactants such as metal surface treatment agents, low-foaming wetting agents, antifoaming agents, or pigment dispersants; and retarders for hydrosilylation reaction on account of their high tendency to form complexes with transition metals, as described in Japanese Patent Publication S44-31476, Japanese Patent Application Laid-Open No. H6-329917 and Japanese Patent Application Laid-Open No. H9-143371.

These acetylene alcohols are generally prepared by reacting a ketone with an acetylide as follows.

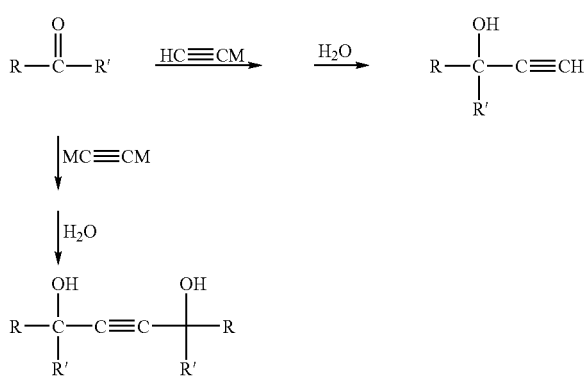

In the above method, a corresponding ketone precursor should be prepared. It may be difficult to prepare such a ketone for an acetylene alcohol having a complicated structure and a high molecular weight.

Meanwhile, Japanese Patent Application Laid-Open No. 2000-53685 discloses a fluorinated organosilicone compound prepared by reacting an acetylene alcohol with a chlorosilane having a fluoroalkyl group. However, the fluorinated organosilicone compound lacks an alcoholic hydroxyl group and thus its performance as a retarder is not satisfactory.

SUMMARY OF THE INVENTION

An object the present invention is to provide a method for preparing an acetylene alcohol which is useful as a retarder, but is difficult to isolate by distillation due to its complicated structure and/or a high molecular weight.

The present invention provides an acetylene alcohol compound represented by the following formula.

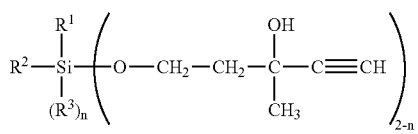

wherein $R^1$ represents a monovalent hydrocarbon group having 4 to 10 carbon atoms with the carbon atom bonded to the silicon atom being a tertiary carbon; $R^2$ and $R^3$ each represents a monovalent group selected from the group consisting of alkyl groups having 1 to 4 carbon atoms and a fluorinated group represented by the formula, Rf—Q—, wherein Rf is a linear or a branched perfluoroalkyl group having 3 to 100 carbon atoms which group may have an ether bond, and Q is a divalent group having 2 to 10 carbon atoms which group may have a nitrogen, an oxygen, or a sulfur atom; and n is zero or 1.

Another aspect of the present invention is a method for preparing a silylated acetylene alcohol comprising the step of reacting the organosilicon compound (A) represented by the following formula, (A)

with the acetylene alcohol (B) represented by the following formula (B)
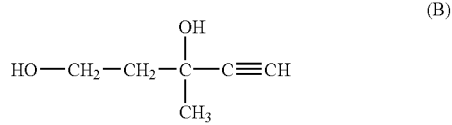

to form an Si—O bond from the Si—X moiety of (A) and the primary hydroxyl group of (B).

The acetylene alcohols of the present invention are very useful as nonionic surfactants, intermediates for chemical synthesis, and retarder for hydrosilylation curing reaction. The acetylene alcohols can be prepared easily with the present method.

DETAILED DESCRIPTION OF THE PREFERRED EMBODIMENTS

Figure 1:
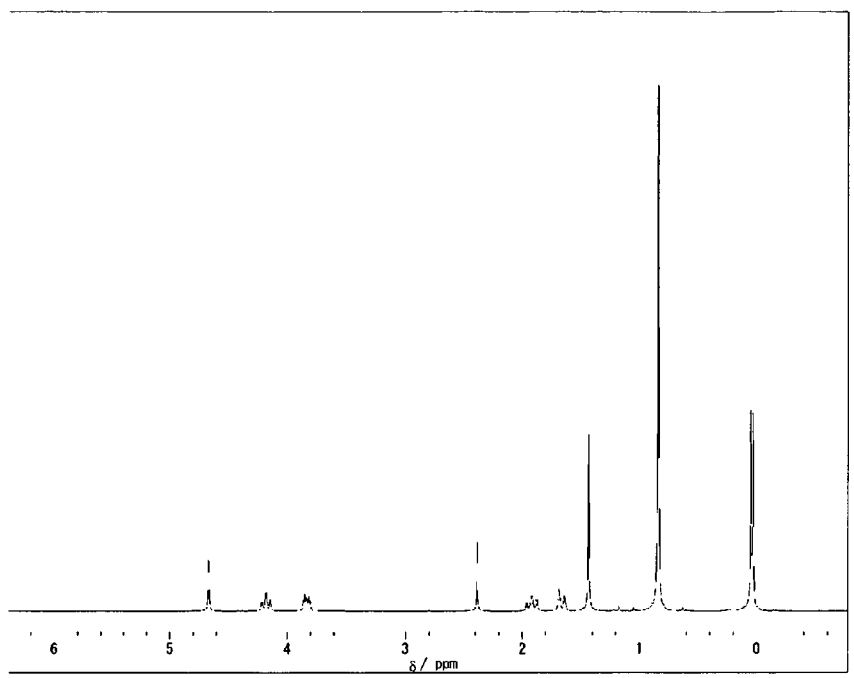
FIG. 1 is a $^1$H-NMR chart of the present acetylene alcohol prepared in Example 1.

In the aforesaid acetylene alcohol compound of the present invention, $R^1$ represents a monovalent hydrocarbon group having 4 to 10 carbon atoms with a carbon atom bonded to the silicon atom being a tertiary carbon. Examples of $R^1$ are as shown below.

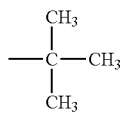 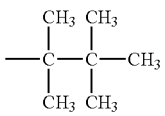 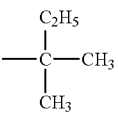

The present acetylene alcohol is characterized by having a bulky functional group bonded to the silicon atom via a tertiary carbon. The bulky functional group is considered to stabilize a Si—O bond, contributing to improve performance as a retarder. A silylated acetylene alcohol without such a bulky substituent group tends to be unstable to be hydrolyzed easily.

$R^2$ and $R^3$ each represents a monovalent group independently selected from the group consisting of alkyl groups having 1 to 4 carbon atoms and a fluorinated group represented by the formula, Rf—Q—, wherein Rf is a linear or a branched perfluoroalkyl group having 3 to 100 carbon atoms which may have an ether bond.

Examples of alkyl groups having 1 to 4 carbon atoms include methyl, ethyl, n-propyl, isopropyl, n-butyl, isobutyl, and t-butyl groups, among which a methyl group is preferred.

Examples of preferred Rf are as follows.

$C_nF_{2n+1}$— n=3–10
$CF_3O$—$(CF_2CF_2O)_n$—$CF_2$— n=1–14
$C_2F_5O$—$(CF_2CF_2O)_n$—$CF_2$— n=0–13

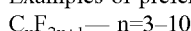
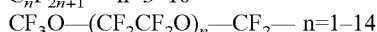
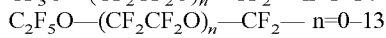

n = 0-30

$C_3F_7O$—$(CF_2CF_2CF_2O)_n$—$CF_2CF_2$— n=0–8
$CF_3O$—$(CF_2CF_2O)_n(CF_2O)_m$—$CF_2$—
   n and m are integers not smaller than 1, with 2n+m being not greater than 30.

Q is an organic group having 1 to 20 carbon atoms which group may have an oxygen atom, for example, a carbonyl group, or a nitrogen atom. Examples of Q are as follows.
   —$(CH_2)_p$— wherein p is an integer of from 1 to 10, preferably 2 to 4;
   —$CH_2$—O— $(CH_2)$ q—

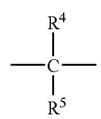

wherein $R^4$ and $R^5$ may be the same with or different from each other and are selected from the group consisting of a hydrogen atom and alkyl groups having 1 to 9 carbon atoms, for example, methyl, ethyl, propyl, phenyl, and cyclohexyl groups; and

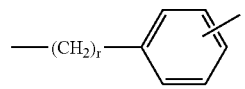

r = 0~4

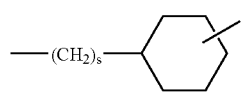

s = 0~4

Preparation Method

The aforesaid acetylene alcohol can be prepared by reacting the organosilicon compound (A) represented by the following formula

wherein $R^1$, $R^2$ and $R^3$ are as defined above and X is a halogen atom, with an acetylene alcohol (B) represented by the following formula

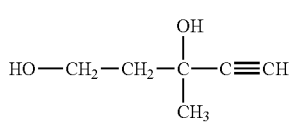

to form a Si—O bond from the Si—X moiety of (A) and the primary hydroxyl group of (B).

Examples of the organosilicon compound (A) are as follows.

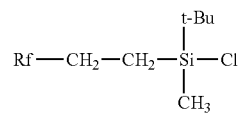

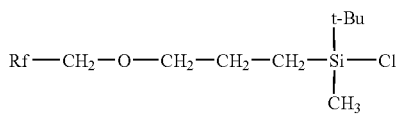

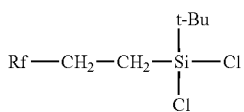

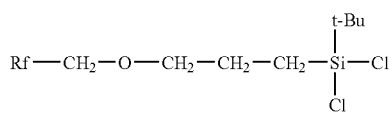

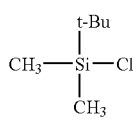

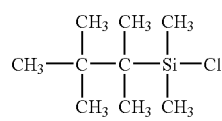

wherein Rf is as described above and t-Bu is a tertiary butyl group.

The organosilicon compound (A) can be prepared by reacting a trihalogenated silane with a Grignard reagent having a bulky group such as t-butyl group. A dihalogenated silane compound thus obtained has the bulky group. By further reacting the dihalogenated silane compound with another Grignard reagent without having a bulky group, a silane compound having a halogen and three substituents can be obtained.

The acetylene alcohol (B) such as 3-methyl-4-pentyne-1,3-diol can be prepared by reacting 4-hydroxy-2-butanone with a Grignard reagent having an acetylene group. It may be prepared by a method described in J. Am. Chem. Soc. 1980, 102, 6255–6259.

The acetylene alcohol of the present invention is prepared by feeding the organosilicon compound (A) to a mixture of the acetylene alcohol (B) and an acid acceptor. Preferred acid acceptors are triethylamine, pyridine, urea, 1,4-diazabicyclo[2,2,2]octane(DABCO), 1,8-diazabicyclo[5,4,7]-7-undecene(DBU), and imidazole.

A solvent may be toluene, xylene, hexane, octane, isooctane, 1,3-bistrifluoromethylbenzene, and N-methylpyrrolidone.

When the organosilicon compound (A) is a monofunctional with n being 1, 1 to 2 moles of the acetylene alcohol (B) and 1 to 3 moles of the acid acceptor are used per mole of the organosilicon compound (A). Reaction may be performed at a temperature of from 20 to 50° C. for 1 to 40 hours. After the reaction, the reaction mixture is repeatedly washed with water and then an organic phase is isolated. An intended acetylene alcohol can be obtained by purifying the organic phase.

When the organosilicon compound (A) is a difunctional with n being 0, 2 to 4 moles of the acetylene alcohol (B) and 2 to 4 moles of the acid acceptor are used per mole of the organosilicon compound (A). Reaction may be performed at a temperature of from 20 to 50° C. for 1 to 20 hours. After the reaction, the reaction mixture is repeatedly washed with water and then an organic phase is isolated. An intended acetylene alcohol can be obtained by purifying the organic phase.

EXAMPLES

The present invention will be further explained in detail with reference to the following Examples, but not limited thereto.

Example 1

In a reactor, 5.00 g, i.e., 0.0439 mole of 3-methyl-3,5-dihydroxy-pentyene, 6.58 g, i.e., 0.0439 mole of t-butyldimethylchlorosilane, 7.50 g, i.e., 0.110 mole of imidazole and 10.0 g of dimethylformamide were placed and subjected to a reaction at room temperature for 20 hours while stirring. After the reaction, 30 g of diethyl ether was added in the reactor and the mixture thus obtained was washed with 50 g of water for 3 times. Subsequently, the mixture was stripped at a temperature of 70° C. and a pressure of 5 mmHg, and 7.2 g of a reaction product was obtained. The product was analyzed by NMR and IR to be found to have the following structure.

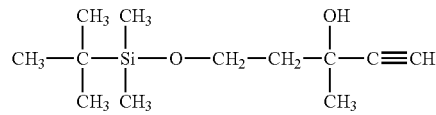

FIG. 1 shows a $^1$H-NMR spectrum of the product dissolved in CDCl$_3$. The peaks observed are listed below with assignment, integrated peak area, and multiplicity shown in parentheses.

δ0.05(Si—CH$_2$, 6H, d)

δ0.84((CH$_3$)$_3$C—Si, 9H, s)

δ1.43(CH$_3$—C—OH, 3H, s)

δ1.63(—OCH$_2$CH$_2$—, 1H, m)

δ1.90(—OCH$_2$CH$_2$—, 1H, m)

δ2.38(—C≡CH, 1H, s)

δ3.83(—OCH$_2$CH$_2$—, 1H, m)

δ4.18(—OCH$_2$CH$_2$—, 1H, m)

δ4.66(—OH, 1H, s)

Figure 2:
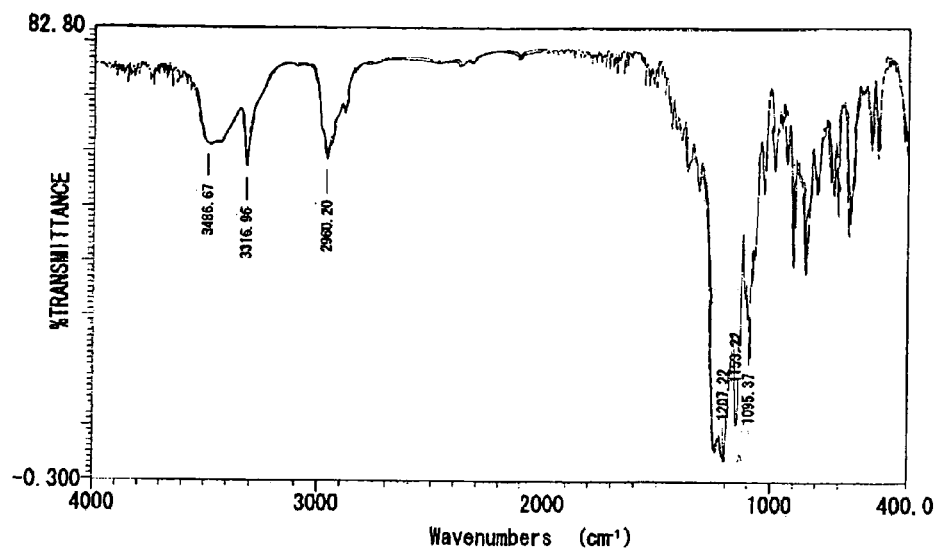
FIG. 2 is an IR chart of the present acetylene alcohol prepared in Example 1.

FIG. 2 shows an IR spectrum of the product. The characteristic absorption bands were as follows.

3478 cm$^{-1}$ (—OH)

3315 cm$^{-1}$ (—CC≡H)

Example 2

In a reactor, 5.0 g of 3-methyl-3,5-dihydroxy-pentyene, 3.2 g of triethylamine, 20 g of 1,3-bistrifluoromethylbenzene and 10 g of the organosilicon compound represented by the following formula

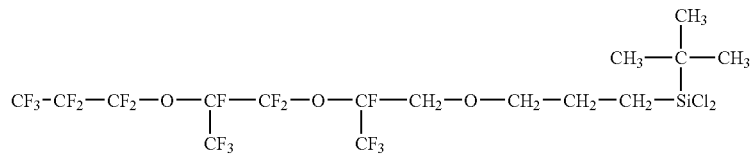

were placed and subjected to a reaction at room temperature for 15 hours while stirring. After the reaction, water was added to the reaction mixture and an organic phase was isolated which then was washed with water for 3 times. To the organic phase, a little amount of anhydrous sodium sulfate was added. After filtering out the sodium sulfate, the organic phase was stripped at a temperature of 100° C. and a pressure of 5 mmHg to remove 1,3-bistrifluoromethylbenzene and 11.3 g of product was obtained. The product was analyzed by NMR and it was found that a major product is represented by the following formula (C) and a little amount of a by-product represented by the following formula (D) was contained.

δ1.53($CH_3$—C—OH, 6H, s)

δ1.80(—$OCH_2$—$CH_2$—$CH_2$, 2H, m)

δ1.80(—$OCH_2CH_2$—, 2H, m)

δ2.06(—$OCH_2CH_2$—, 2H, m)

δ2.47(—C≡CH, 2H, m)

δ3.56(—$OCH_2$—$CH_2$—$CH_2$, 2H, m)

δ3.98(CF—$CH_2$—O, 2H, d)

δ4.15(—$OCH_2CH_2$—, 2H, m)

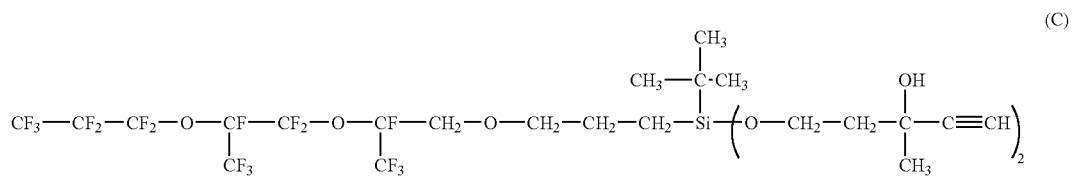

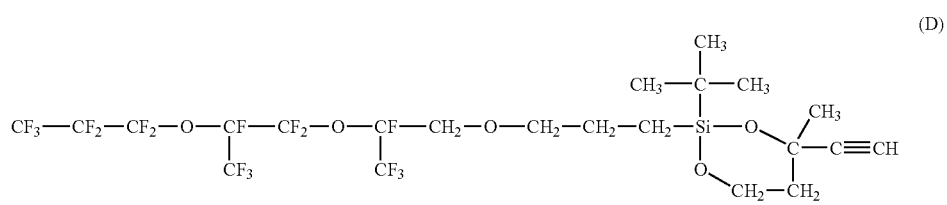

Figure 3:
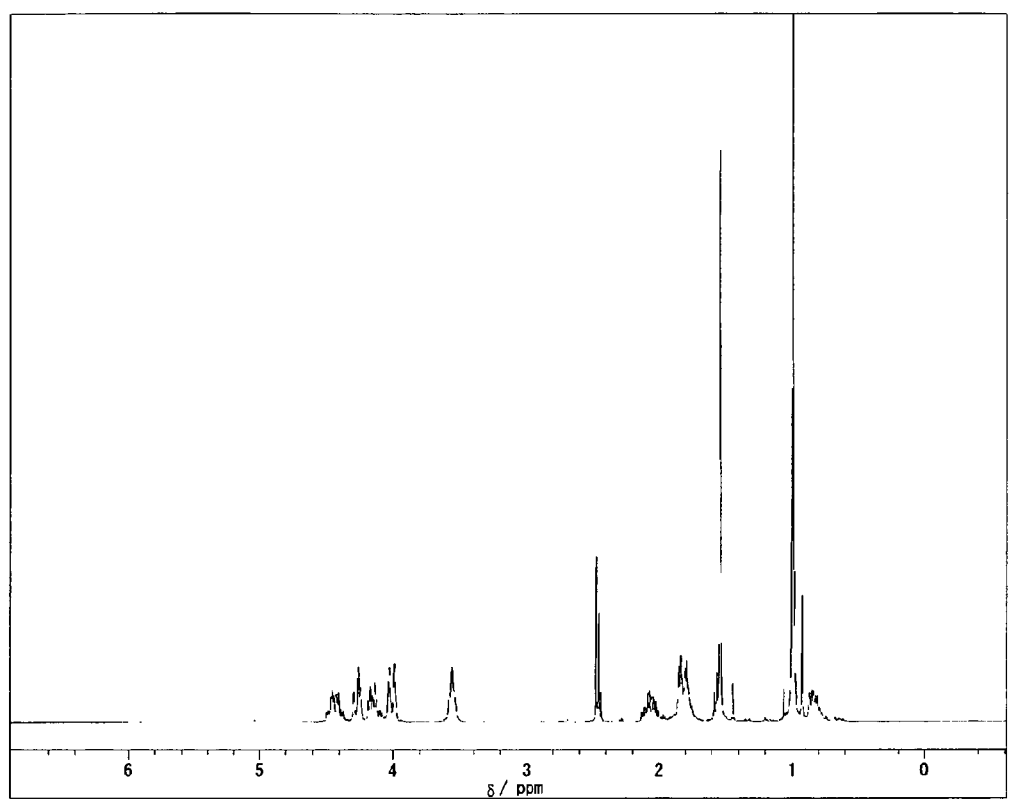
FIG. 3 is a $^1$H-NMR chart of the present acetylene alcohol prepared in Example 2.

FIG. 3 shows a $^1$H-NMR spectrum of the product dissolved in $CDCl_3$. The peaks observed are listed below with assignment, integrated peak area, and multiplicity shown in parentheses.

δ0.82(Si—$CH_2$, 2H, s)

δ0.99(($CH_3$)$_3$C—Si, 9H, s)

δ4.25(—OH, 2H, m)

δ4.43(—$OCH_2CH_2$—, 2H, m)

Figure 4:
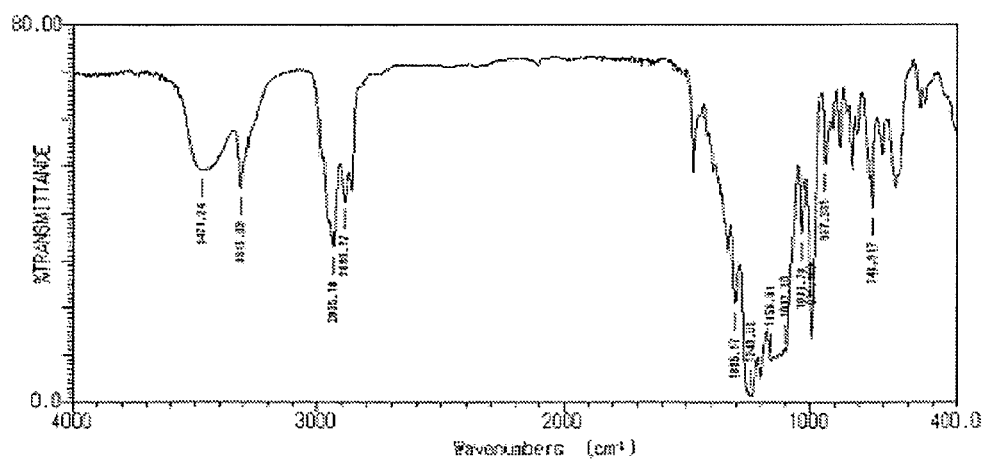
FIG. 4 is an IR chart of the present acetylene alcohol prepared in Example 2.

FIG. 4 shows an IR spectrum of the product. The characteristic absorption bands were as follows.

3478 cm$^{-1}$ (—OH)

3315 cm$^{-1}$ (—C≡CH)

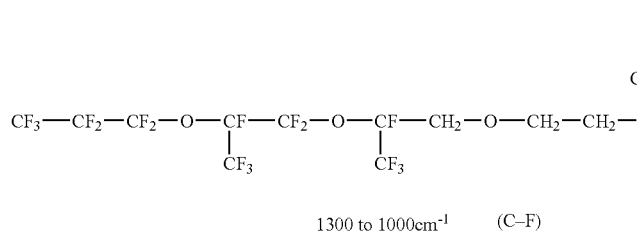

(D)

1300 to 1000cm$^{-1}$  (C–F)

The invention claimed is:

1. An acetylene alcohol represented by the following formula,

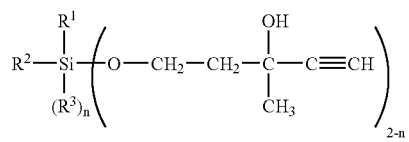

wherein $R^1$ represents a monovalent hydrocarbon radical having 4 to 10 carbon atoms with the carbon atom bonded to the silicon atom being a tertiary carbon, $R^2$ and $R^3$ each represents a monovalent group selected from the group consisting of alkyl groups having 1 to 4 carbon atoms and a fluorinated group represented by the formula, Rf—Q—, wherein Rf is a linear or branched perfluoroalkyl group having 3 to 100 carbon atoms which may be interrupted by one or more ether bonds, and Q is a divalent group having 2 to 10 carbon atoms which may be interrupted by one or more nitrogen, oxygen, or sulfur atoms, and n is zero or 1.

2. A method for preparing a silylated acetylene alcohol comprising the step of reacting the organosilicon compound (A) represented by the following formula

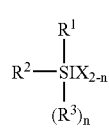 (A)

wherein $R^1$ represents a monovalent hydrocarbon radical having 4 to 10 carbon atoms with the carbon atom bonded to the silicon atom being a tertiary carbon, $R^2$ and $R^3$ each represents a monovalent group selected from the group consisting of alkyl groups having 1 to 4 carbon atoms and a fluorinated group represented by the formula, Rf—Q—, wherein Rf is a linear or a branched perfluoroalkyl group having 3 to 100 carbon atoms which may be interrupted by one or more of ether bonds and Q is a divalent group having 2 to 10 carbon atoms which may be interrupted by one or more of nitrogen, oxygen, or sulfur atoms, X is a halogen atom and n is zero or 1, with the acetylene alcohol (B) represented by the following formula

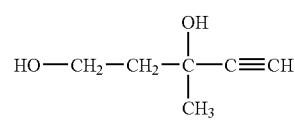 (B)

to form an Si—O bond from the Si—X moiety of (A) and the primary hydroxyl group of (B).

\* \* \* \* \*